United States Patent
Laghi

(10) Patent No.: US 7,709,570 B2
(45) Date of Patent: May 4, 2010

(54) SURFACE MODIFICATION OF TRIBLOCK COPOLYMER ELASTOMERS

(75) Inventor: Aldo A. Laghi, Clearwater, FL (US)

(73) Assignee: Alps South, LLC, Clearwater, FL (US)

( * ) Notice: Subject to any disclaimer, the term of this patent is extended or adjusted under 35 U.S.C. 154(b) by 756 days.

(21) Appl. No.: 11/242,815

(22) Filed: Oct. 3, 2005

(65) Prior Publication Data

US 2006/0111485 A1   May 25, 2006

Related U.S. Application Data

(63) Continuation-in-part of application No. 10/817,612, filed on Apr. 2, 2004, now abandoned, and a continuation-in-part of application No. 10/907,472, filed on Apr. 1, 2005, now abandoned.

(51) Int. Cl.
*C08K 5/01* (2006.01)
*C08L 53/00* (2006.01)

(52) U.S. Cl. .................. 524/474; 524/147; 524/342; 524/349; 524/351; 524/352; 523/122

(58) Field of Classification Search ............... 524/147, 524/342, 349, 351, 352, 474; 523/122
See application file for complete search history.

(56) References Cited

U.S. PATENT DOCUMENTS

| | | | | |
|---|---|---|---|---|
| 4,369,284 A | * | 1/1983 | Chen | 524/476 |
| 6,852,776 B2 | * | 2/2005 | Ong et al. | 523/122 |
| 7,053,145 B1 | * | 5/2006 | Tasaka et al. | 524/436 |
| 2005/0101693 A1 | * | 5/2005 | Arbogast et al. | 523/122 |
| 2006/0020061 A1 | * | 1/2006 | Knoll et al. | 524/111 |

* cited by examiner

*Primary Examiner*—Peter Szekely
(74) *Attorney, Agent, or Firm*—Henry J. Recla

(57) ABSTRACT

Thermoplastic elastomers may be manufactured by mixing together plasticizing oil, a triblock copolymer and one or more additives, e.g., an antioxidant, an antimicrobial agent, and/or other additives, to form a mixture which is melted then cooled into the thermoplastic elastomer. During cooling the thermoplastic elastomer may be molded or otherwise formed into any number of articles including, but not limited to, prosthetic liners, prosthetic sleeves, external breast prostheses, breast enhancement bladders, wound dressing sheets, wound dressing pads, socks, gloves, malleolus pads, metatarsal pads, shoe insoles, urinary catheters, vascular catheters and balloons for medical catheters both vascular as well as urinary.

18 Claims, 13 Drawing Sheets

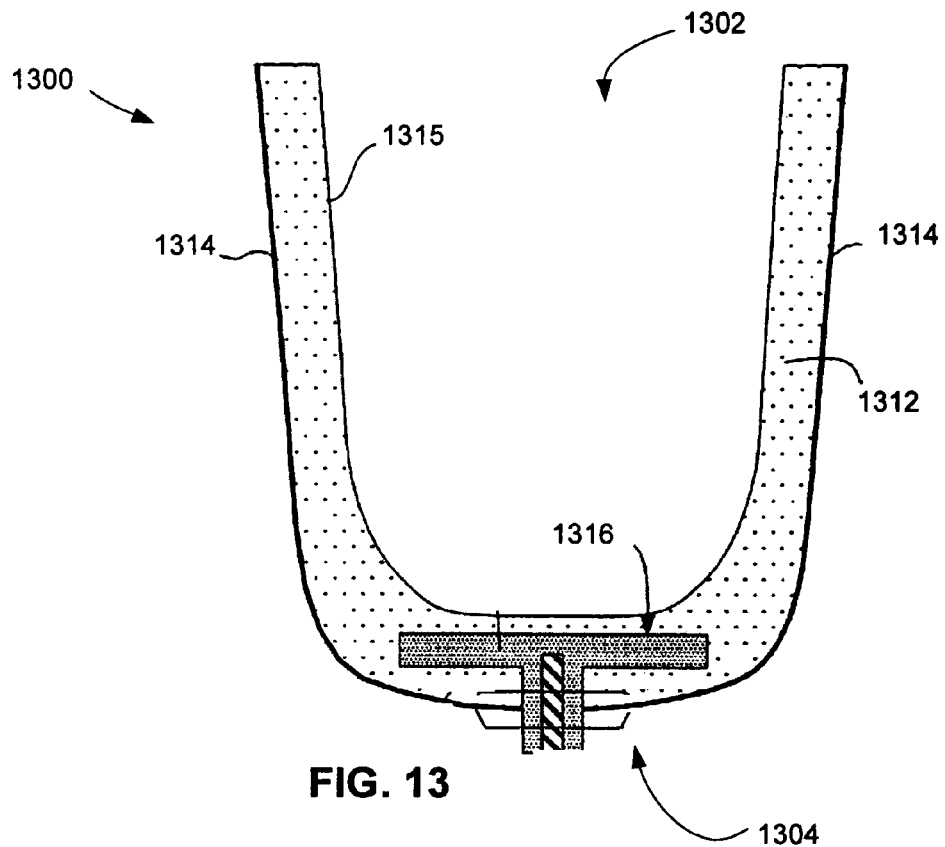
FIG. 13
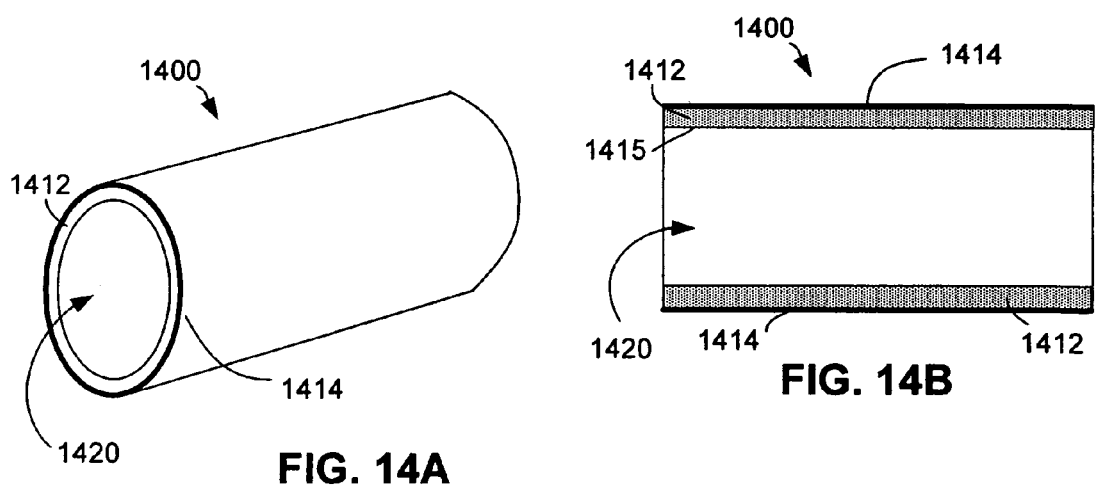
FIG. 14A
FIG. 14B

SURFACE MODIFICATION OF TRIBLOCK COPOLYMER ELASTOMERS

1.0 CROSS REFERENCE TO RELATED APPLICATIONS

This application is a continuation in part of U.S. patent application Ser. No. 10/817,612 filed Apr. 2, 2004 now abandoned, entitled "Precipitation of additives in over-saturated triblock copolymer elastomers", and of U.S. patent application Ser. No. 10/907,472, filed Apr. 1, 2005 now abandoned, entitled "Antimicrobial Articles and Compositions Made from Thermoplastic Elastomers", both of which are incorporated by reference herein in their entireties.

2.0 BACKGROUND

1. Field of the Invention

This invention relates to a thermoplastic elastomer having improved surface characteristics for skin contact applications, pressure ulcers and wound management.

2. Background of the Invention

U.S. Pat. No. 4,678,664 discloses a gel composition that includes water, mineral oil and two polyoxyethylene-polyoxybutylene block copolymers designated copolymer A and copolymer B. The block copolymers are cogeneric mixtures of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms.

U.S. Pat. No. 4,369,284 discloses a gelatinous composition that contains an intimate melt blend admixture of poly(styrene-ethylene-butylene-styrene) triblock copolymer having a styrene end block to ethylene and butylene center block ratio within the range of 31:69 to 40:60, and high levels of a plasticizing oil. The gelatinous composition is transparent and has a combination of properties including high elongation and tensile strength and shape retention after deformation under velocity impact and stress conditions. The gelatinous products of this invention are soft, flexible, and have elastic memory, characterized by a gel rigidity of from about 20 gram to about 700 gram Bloom.

Products made from these gelatinous compositions tend to rupture and crumble when under shearing stress conditions. Moreover, these prior methods and products do not have certain surface characteristics of elastomers which are beneficial in a variety of applications. More particularly, if used in applications where the composition is in prolonged contact with human skin, the friction produced by such products, coupled with a lack of sufficient lubrication, can produce patient discomfort.

What is needed is an improved method of making an elastomer composition where the surface characteristics of the elastomer are beneficial in skin contact applications. Specifically, the needed elastomer composition would provide enhanced patient comfort and satisfaction when used in applications that include prolonged skin contact.

3.0 SUMMARY OF THE INVENTION

The present invention overcomes the disadvantages of the current art and provides a durable elastomer having improved surface characteristics and enhanced utility in applications involving sustained contact with human skin. The thermoplastic elastomers of the invention have microcraters on their surface, formed by the precipitation of additives, such that the surface is smooth to the touch and low friction to the skin, but which provides a surface of increased surface area relative to surfaces without such microcraters. Such increased surface area provides advantages in that, for example, such a surface can incorporate increased amounts of a therapeutic or antimicrobial agents related to a surface without such microcraters.

In some embodiments, thermoplastic elastomers of the present invention may be manufactured by mixing together plasticizing oil, a polymer and one or more additives, e.g., an antioxidant, an antimicrobial agent, and/or other additives, to form a mixture which is melted then cooled into the thermoplastic elastomer. Alternatively, the one or more additives may be added to the mixture after the mixture is melted or during the cooling process. During cooling the thermoplastic elastomer may be molded or otherwise formed into any number of articles including, but not limited to, prosthetic liners, prosthetic sleeves, external breast prostheses, breast enhancement bladders, wound dressing sheets, wound dressing pads, socks, gloves, malleolus pads, metatarsal pads, shoe insoles, urinary catheters, vascular catheters and balloons for medical catheters both vascular as well as urinary.

In some embodiments, the polymer comprises a triblock copolymer comprising styrene and at least one of ethylene, butadiene, butylene, propylene, or isoprene, for example a styrene-ethylene-ethylene-propylene-styrene, a styrene-ethylene-butylene-styrene, or a styrene-ethylene-propylene-styrene. In certain embodiments, thermoplastic elastomers according to the present invention comprises a polymer that is a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprene/butadiene-b-styrene), or combinations thereof. In certain embodiments, the thermoplastic article comprises any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

Thermoplastic elastomers of the present invention also comprise selected amount of one or more plasticizing oils, for example, a paraffinic oil, naphtenic oil, a mineral oil, or a synthetic liquid oligomer of a polybutene, a polypropene, or a polyterpene oil. The plasticizing oil may be heated prior to mixing the additive and polymer therewith, but such heating is not strictly necessary. An extruder, a molding machine, or other similar heated vessel is used to accomplish the above-mentioned melting of the mixture so that the additive(s) become melted and soluble in the molten mixture.

A thermoplastic elastomer comprises one or more additives, such as antioxidants or hydroxyl scavengers, that optimize the surface characteristic of the elastomer. Such additives may be in a stable solution with a mixture of polymer and plasticizing oil when the mixture is in its molten state. An elastomer is formed when the molten mixture cools and solidifies. As the mixture cools down the solubility of the additives decreases and the mixture becomes a supersaturated solution. When solidification is complete, the additives begin to precipitate from the elastomer. The additives migrate, for example through a process of diffusion, to the surface of the elastomer where they create microcraters, pits or other imperfections or features on the surface of the elastomer. The migrated additives may also form a dry layer of microscopic powder on the elastomer surface. The microcraters and/or the powdery interface may improve the comfort of the user and enables the elastomer to remain in contact with the user's skin for prolonged periods of time. Even if the surface is wet, the micro-craters may collect small pools of liquid that provide lubricity. In embodiments wherein the thermoplastic elastomer is used to promote wound healing, the additive is preferably an antioxidant or free radical scavenger.

In some embodiments, the present invention provides a composition for controlling microbial activity with skin contact applications and for treating wounds including a thermoplastic elastomer comprising a dispersion of antioxidants and/or antimicrobial agents within the thermoplastic elastomer. The thermoplastic elastomers may also have a predetermined modulus sufficient to maintain a substantially uniform pressure on a wound. Application of such a thermoplastic elastomer over a wound or the skin permits the migration of hydroxyl scavengers and/or antimicrobial agents from the surface of the elastomer to the skin. The presence of such compounds may aid in wound healing and/or keep the skin and wound site free of infection.

In some embodiments, antimicrobial agent additives may include any of silver zeolite, silver zirconium phosphate, silver nitrate, silver thiosulfate, silver sulphadiazine, silver fusidate, and quaternary ammonium compounds (QAC). Other classes of silver-based antimicrobial agents may be used as well, for example a silver acetate, a silver bromide, a silver carbonate, a silver chlorate, a silver chloride, a silver citrate, a silver fluoride, a silver iodate, a silver lactate, a silver nitrate, a silver nitrite, a silver perchlorate or a silver sulfide. One or more other antimicrobial agents may be used in conjunction with or instead of such silver-based antimicrobial agents.

In other embodiments, thermoplastic elastomers of the present invention may be impermeable to water whereby retention of moisture to a wound and skin is achieved. The soft nature of the elastomer may enable controlled compression of the wound to prevent ischemia. The soft nature of the elastomer also minimizes frictional and shear forces on the skin. As a consequence tissue necrosis may be virtually eliminated.

4.0 BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 13 is a diagram of a cross-sectional view of a prosthetic liner comprising a thermoplastic elastomer of the present invention.

FIG. 14A is a perspective view of a prosthetic sleeve comprising a thermoplastic elastomer of the present invention.

FIG. 14B is a cross-sectional view of the prosthetic sleeve of FIG. 14A.

5.0 DETAILED DESCRIPTION

Figure 1:
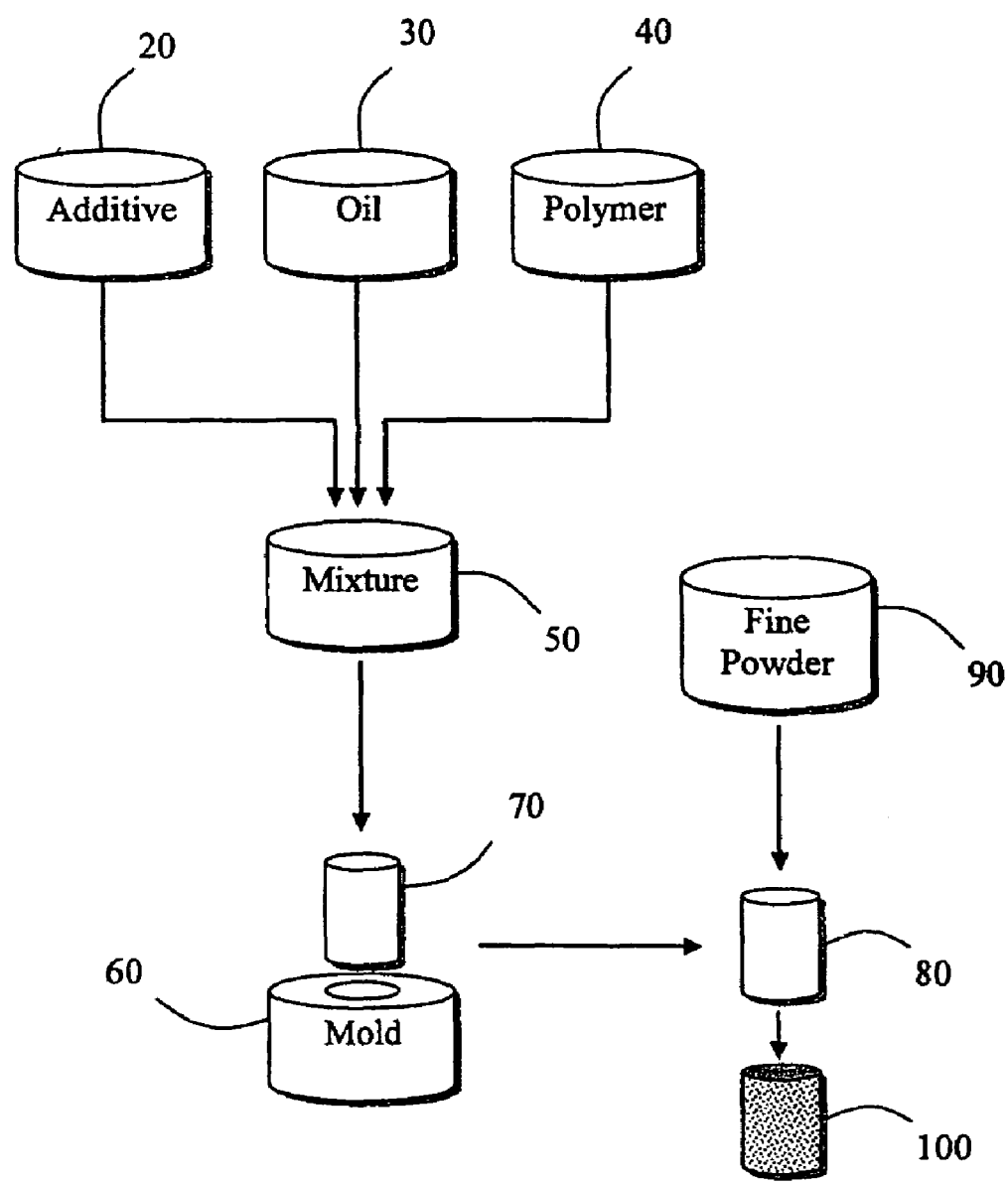
FIG. 1 is a diagrammatic view of an embodiment of the invention.

Referring to FIG. 1, thermoplastic elastomers having improved surface characteristics may comprise a mixture 50 of one or more polymers, preferably triblock copolymers 40, a plasticizing agent or oil 30, and one or more additives 20. Suitable elastomeric materials include, for example, styrenic triblock copolymers, such as a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprene/butadiene-b-styrene), or combinations thereof. In certain embodiments, elastomeric articles of the present invention comprise any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

Suitable oils 30 include plasticizing oils such as paraffinic oils, naphtenic petroleum oils, mineral oils, and synthetic liquid oligomers of polybutene, polypropylene, polyterpene, etc. may be used. Optionally, a seeding of the oil may also be effected, with an insoluble fine powder such as talc. In some embodiments, 300 to 1000 parts by weight of the plasticizing oil are used, more preferably between about 500 and 700 parts per hundred (PPH) of triblock copolymer.

The oil 30 or other plasticizing agent (also referred to herein as a plasticizer) can be added to the triblock copolymer 40 in order to provide desired mechanical properties, such as elasticity, softness (or hardness), and elongation, tear and tensile strength characteristics of the resulting elastomer. For example, in some embodiments, suitable mechanical properties of the resulting elastomer include: (a) hardness between approximately 10 to 70 durometer on the Shore 00 scale, more preferably about 25 durometer on the Shore 00 scale; (b) ultimate elongation of approximately 300 to 2000 percent, more preferably about 1500 percent; and/or (c) tensile modulus at 300 percent elongation of between about 5 to 300 psi, more preferably about 30 psi.

One or more other additives 20 are also included, that precipitate out of a molten mixture of the polymer, plasticizing oil, and additive, upon cooling, thereby forming microcraters on the surface of the resulting thermoplastic elastomer. Preferably, the surface microcraters have an average radius of between about 0.001 mm and 0.07 mm, more preferably between about 0.0067 mm and 0.0433 mm, and an average depth between about 0.0183 mm and 0.1434 mm, for example to provide a desired tactile feel, and/or to optimize surface characteristics, mechanical properties or other characteristics of the resulting thermoplastic elastomer. The additive is a compound that has lower solubility in the mixture of polymer and plasticizing oil when cooled to room temperature (e.g., about 25° C.), than at the higher than room temperature at which the mixture of polymer and plasticizing oil and additive are all in solution. In preferred embodiments, additives 20 comprise one or more antioxidants and/or antimicrobial agents.

Table 1 includes examples of suitable antioxidant additives.

TABLE 1

Antioxidant Additives

Chemical Name

1 Tetrakis (2,4-di-tert-butylphenyl) [1,1-biphenyl]-4,4'-diylbisphosphonite
2 Tris (2,4-di-(tert)-butylphenyl) phosphite [e.g., IRGAFOS 168, Ciba Chemicals, Inc., Tarrytown, NY]
3 Butanedioic acid, dimethylester, polymer with 4-hydroxy-2,2,6,6-tetramethyl-1-piperidine ethanol
4 2,6-di-tert-butyl-4-(4,6-bis(octylthio)-1,3,5-triazin-2-ylamino) phenol
5 3,3',3'',5,5',5''-hexa-tert-butyl-a,a',a''-(mesitylene-2,4,6-triyl) tri-p-cresol
6 Pentaerythritol Tetrakis (3-(3,5-di-tert-butyl-4-hydroxphenyl)propionate) [e.g., IRGANOX 1010, Ciba Chemicals, Inc., Tarrytown, NY]

TABLE 1-continued

Antioxidant Additives

Chemical Name

7 Phenol, 2-(5-chloro-2H-benzotriazole-2-yl)-6-(1,1-dimethylethyl)-4-methyl
8 Thiodiethylene bis(3-(3,5-di-tert-butyl-4-hydroxyphenyl)propionate)
9 Calcium phosphonate
10 Dioctadecyl 3,3'-thiodipropionate
11 Didodecyl 3,3'-thiodipropionate
12 2-(1,1-dimethylethyl)-6-[[3-(1,1-dimethylethyl)-2-hydroxy-5-methylphenyl]methyl-4-methylphenyl acrylate
13 N,N'-hexane-1,6-diylbis(3-(3,5-di-tert-butyl-4-hydroxyphenylpropionamide))

The tris (2,4-ditert-butylphenyl) phosphate as listed in Table I is a white crystalline powder, commonly used as a phosphate processing stabilizer for polycarbonate and polyolefins. It can be used in combination with phenolic antioxidants and acts for synergistical color stability and polymer viscosity. The butanedionic acid as listed in Table I, also known as succinic acid, is a dicarboxylic acid with four carbon atoms, occurs naturally in plant and animal tissues and can play a role in intermediary metabolism (Krebs cycle). It is a colorless crystalline solid with a melting point of 185-187° C., soluble in water, slightly dissolved in ethanol, ether, acetone and glycerine, but not dissolved in benzene, carbon sulfide, carbon tetrachloride and oil ether. A common method of synthesis of succinic acid is the catalytic hydrogenation of maleic acid or its anhydride. Succinic acid has uses in certain drug compounds, in agricultural and food production, and in perfume esters. In a preferred embodiment, pentaerythritol tetrakis(3-(3,5-di-tert-butyl-4-hydroxphenyl)propionate) is the additive used.

In some embodiments, 0.5 to 10 parts per hundred (PPH) of one or more additives can be mixed with the plasticizing oil or with the plasticizing oil and polymer mixture. More preferably, additive 30 is used in a amount of 0.45%-0.7%, based upon the total weights of polymer 40 plus mineral oil 30 plus additive 20. Using a percent may be more preferably to parts, or PPH, as the ratio of oil to polymer can change considerably. The additives can be solid at room temperature (25° C.) and soluble in the molten mixture. The additives have higher solubility in the triblock copolymer elastomers at higher temperatures than at room temperature. The addition of such additives can be in a predetermined proportion that exceeds the solubility of the additives 20 in the elastomer at room temperature. The addition of such additives to the mixture 50 of polymers 40 and plasticizing oil 30 can be made either prior to the melting of the mixture in a heated vessel or when the mixture is in its molten state.

In embodiments where the additive comprises an antimicrobial agent, suitable antimicrobial agent additives include but are not limited to silver zeolite, silver zirconium phosphate, silver nitrate, silver thiosulfate, silver sulphadiazine, silver fusidate, and quaternary ammonium compounds (QAC). Other classes of silver-based antimicrobial agents may be used as well, for example a silver acetate, a silver bromide, a silver carbonate, a silver chlorate, a silver chloride, a silver citrate, a silver fluoride, a silver iodate, a silver lactate, a silver nitrate, a silver nitrite, a silver perchlorate or a silver sulfide. One or more other antimicrobial agents may be used in conjunction with or instead of such silver-based antimicrobial agents or other additive.

Modulus of elasticity, measured at 300% elongation, for the softer formulations of this elastomer are generally in the range of about 5 psi to 50 psi, exhibiting elongations at break in the range of 1500% to 2500%. The modulus of elasticity for a material is the ratio between the force required to stretch the material to a given length (represented as a percentage of its original length) and the cross section of the material prior to stretching. For example, the force required for 0% elongation is 0, values increase in substantially linear relation as force is applied to any given material. Accordingly, the higher the modulus the stiffer the material. The modulus is inversely proportion to the amount of plasticizing oil in the composition of the elastomeric gel. Table 1 provides the modulus for various concentrations of plasticizing oil (as measured by parts oil by weight per 100 parts of the polymer) in the novel composition.

TABLE 2

Tensile modulus characteristics

| PHR oil (parts oil by weight per 100 parts of polymer) | %300 Modulus (tensile modulus PSI measured at 300% elongation) |
|---|---|
| 300 | 55 |
| 400 | 44 |
| 500 | 35 |
| 600 | 24 |
| 700 | 15 |
| 800 | 8 |

5.1 Methods of Making a Thermoplastic Elastomer with Surface Modifications Using Additives Referring again to FIG. 1, a method of making a thermoplastic elastomer according to an embodiment can include mixing additive 20, plasticizing oil 30 and polymer 40 to form a mixture 50. One or more additives such as antioxidant or hydroxyl scavenger additives, e.g., such as one or more of those additives listed in Table I above, are used to create a powder-like precipitate that diffuses to the surface of the elastomer during and/or after formation to create surface microcraters that reduce tackiness of the elastomer where such surface characteristics are desired.

Plasticizing oil 30 may be heated prior to the addition of polymer 40 and/or additive 20. Mixture 50 can be melted, for example in an extruder, a molding machine or other suitable heated vessel so that the additives become soluble in molten mixture 50 and remain in stable solution in the molten mixture 50.

Molten mixture 50 can then be molded 60 or otherwise shaped into any desired shape or form, for example into a prosthetic sleeve or liner configured to receive the residual limb on an amputee (e.g., of an arm or leg) or a front or rear prosthetic breast skin. When allowed to cool, the mixture can solidify and form elastomer 80. The additives can begin to diffuse to the surface of elastomer 80 upon completion of the solidification process. Precipitation optionally may be initiated by seeding the surface of elastomer 80 with fine powder 90 such as talcum powder, for example during the cooling process. Elastomer 80 can then be cooled to solidify elastomer 100, whereby additive 20 may precipitate to the surface of solidified elastomer 100, e.g., in the form of a dry powder.

If the plasticizing oil is heated, an appropriate temperature range may be about 130 to 165° F. As described above, plasticizing oils such as paraffinic oils, naphtenic petroleum oils, mineral oils, and synthetic liquid oligomers of polybutene, polypropylene, polyterpene, and the like may be used. Optionally, a seeding of the oil may also be effected, with an insoluble fine powder such as talcum powder. Preferably, 300 to 1000 parts by weight, more preferably 500 to 700 parts per weight, of the plasticizing oil may be used.

An additive 20 can then be mixed in the plasticizing oil, optionally with seed, for a defined time, e.g., approximately 5 to 15 minutes, more preferably about 10 minutes, at a temperature of approximately 130 to 165° F. One or more additives 20 may also be added to the plasticizing oil 30 with or after the addition of the polymer 40.

In a specific embodiment, a polymer 40 or mixture of polymers is added to the plasticizing oil 30 or to the mixture of plasticizing oil and additives for a desired period of time, for example 20-40 minutes, more preferably about 30 minutes, at 130° F. to 165° F. starting temperature. As described above, suitable polymers may be any triblock copolymer, including for example styrenic triblock copolymers such as SEP, SEPS, SEBS or SEEPS. Preferably, 100 parts by weight of one or a mixture of two or more of a hydrogenated styrene/isoprene/butadiene block copolymer are used.

The mixture containing the plasticizing oil, the additive and the polymer can be melted in an extruder, a reciprocating screw molding machine, or a heated vessel at about 400 to 460° F., more preferably between about 415° F., for example. As mentioned earlier, the additive may be added to the mixture of polymers and plasticizing oils either prior to the melting of the mixture or in the melt phase.

After melting, the mixture is maintained at an elevated temperature, with or without mixing, for an amount of time necessary to ensure adequate dissolution and dispersion of the additives in the mixture. The time required to effect an adequate mixture is function of the triblock copolymer used and the equipment used to melt the mixture. For high molecular weight copolymers, such as Septon 4055 the time at temperature is considerably higher than for lower molecular weight copolymer such as Septon 4033. Also reciprocating screw type injection molding machines or plastic extruders require less time at temperature than melting pots or vats. Also, when using melting pots and vats the time at temperature can be dependent on the size of the pot. Thus, in some embodiments utilizing high molecular weight polymers, a typical time for processing the mixture is, for example, 10 to 30 minutes in a reciprocating screw type injection molding machine or an extruder, and 4 to 16 hours in a melting pot or vat. In embodiments utilizing low molecular weight polymers, a typical time for processing the mixture is, for example, 5 to 15 minutes in a reciprocating screw, and 2 to 8 hours in a melting pot or vat.

After the expiration of such amount of time, the mixture can be molded or extruded or cast and then allowed to cool or can be actively cooled. In either event, the mixture may undergo a phase change from liquid to semi-solid or solid. The additives can remain dissolved in the molten mixture, where upon solidification of the mixture, the mixture becomes an elastomer and precipitation of the additives from the elastomer begins.

More particularly, where the mixture is first melted and then cooled, at a controlled temperature profile, precipitation of the additives can occur within the elastomer as the solubility parameters of the additive in the elastomer are exceeded. The solubility of the additives can decrease as the temperature of the elastomer falls. Precipitation may be initiated by seeding the surface of the elastomer with a fine powder such as talcum powder. Precipitation may also be initiated or facilitated by mechanical solicitation of the elastomer, such as stretching or other deformation of the elastomer. In a specific embodiment, placing the elastomer at room temperature allows sufficient cooling to form microcraters of the desired size; and precipitation can also be initiated by deforming or mechanically stressing (e.g., rubbing, stretching, bending) the elastomer at room temperature, e.g., after contacting is with a precipitation seed such as talcum powder.

The size of the particles of the precipitated phase can be a function of the time temperature profile maintained during the cooling period and of the mechanical stress to which the elastomer is subjected. More particularly, the particles may increase in size as the cooling rate is decreased and as the amount of mechanical deformation is decreased. A faster cooling rate (e.g., under refrigeration instead of room temperature) and greater mechanical deformation can produce smaller particle sizes.

The diffusion rate of precipitate to the surface of the liner can also increase as the stress to strain ratio decreases, i.e., the diffusion rate increases as the modulus of the elastomer, or elastic limit stress, decreases.

Molding, casting or extruding of the molten mixture can be conducted at a mold temperature of, for example, 95-130° F. for 5-10 minutes. The molded elastomer can be removed from the mold after the expiration of such period of time. Although stretching is not required, stretching of the elastomer by about 50% may improve the diffusion rate. Other mechanical deformation of the elastomer may be substituted for or added to the stretching.

The step of aging at a controlled temperature profile may also be performed. For example, such aging may be accomplished at a temperature of 20-32° C. for one (1) hour to 48 hours, more preferably about 24 hours. For example, FIG. 5 shows a photograph of an elastomer before (left) and after (right) aging at room temperature, e.g., approximately 25° C. for 24 hours.

Figure 5:
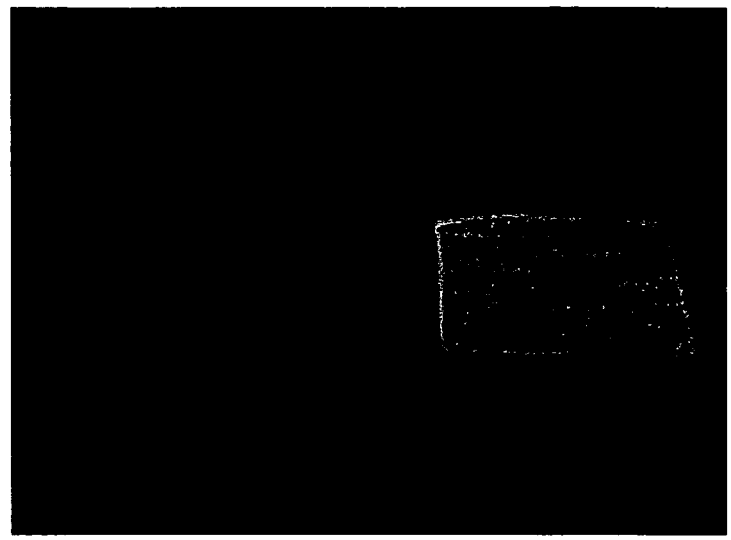
FIG. 5 is a photograph of a thermoplastic elastomer before precipitation of additives (left) and after precipitation of additives (right).

The precipitated phase can diffuse to the surface of the elastomer and collect as a powder on its surface as shown in the right photo of FIG. 5. After optional removal of the surface powder, by wiping, washing (e.g., using a washing machine), or the like, additional powder can migrate to the surface of the elastomer. The process can be repeated until the saturation level at room temperature of the precipitate phase in the elastomer is reached. The process of diffusion to the surface may then stop.

Figure 2:
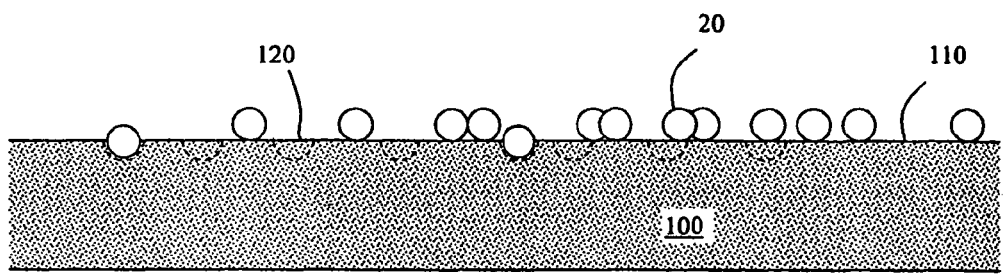
FIG. 2 is a side-elevated, partially sectional diagrammatic view of the elastomer surface according to an embodiment of the invention.

As illustrated in FIG. 2, the diffusion has several advantageous characteristics. The diffused precipitated phase modifies the surface characteristics of elastomer 100 by creating micro-craters 120 on elastomer surface 110. The average number of microcraters per unit can vary depending upon, for example, by the amount of antioxidant additives that are used, the speed of cooling, and/or by imparting mechanical stresses on the elastomeric material during the cooling process. When the precipitation occurs quickly, the microcraters are more numerous, smaller and more packed. When the partials fall out of solution slowly they are larger and more spaced. If the process of precipitation of the hydroxyl scavengers occurs too slowly, the scavengers coagulate together to form crystals on the surface of the elastomer. The crystals and/or the resulting microcraters make the surface rough and may be undesirable for use in skin contact applications.

The depth of the microcraters can vary with the number and size of particles that have emerged from the precipitation. The precipitated and migrated particles may stack on top of each other at the surface of the elastomer, forming a variable depth. The range of depth of surfaces having desirable characteristics, may be, for example 0.005 mm to 0.2 mm, more preferably between about 0.018 mm and 0.143 mm.

The diffusion has several advantageous characteristics. The diffused precipitated phase modifies the surface characteristics of the elastomers by creating micro-craters on the surface as seen in the photographs of FIGS. 6-12, which are described herein in detail in Examples, Section 6.1.

Figure 3:
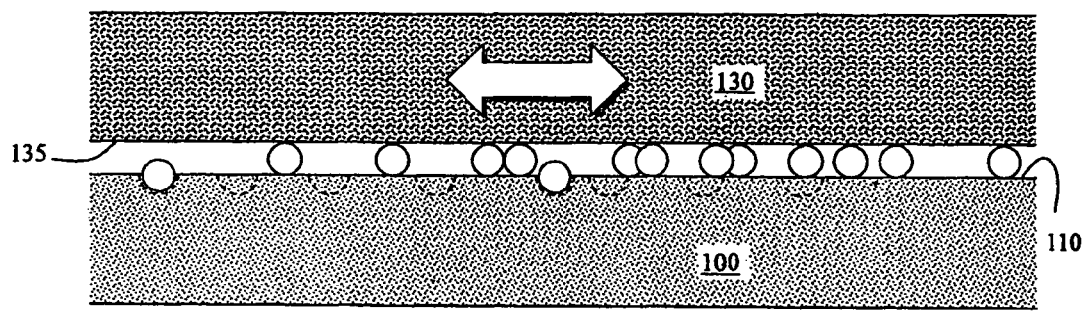
FIG. 3 is a side-elevated, partially sectional diagrammatic view of the elastomer surface in contact with an epidermal surface according to an embodiment of the invention.

The surface modifications achieved by the novel method reduce the friction between the skin or other human tissue and the elastomer and increase the surface area of the elastomer's surface. Referring to FIG. 3, epidermal tissue 130 having skin surface 135 abuts molded surface 110 whereby precipitated additive 20 reduces lateral movement friction. Thus a lubricant may be added to molded surface 110 and retained by micro-craters 120 prior to contact with epidermal tissue 130. This is an advantageous feature in applications such as burn patient treatment applications, scar reduction pads, wound care dressings, goggle frames, masks, headbands, orthotics, prosthetics, garments, urinary catheters, temporary implantations, and applications of cosmetics. Other applications not expressly mentioned herein are also within the scope of this invention as a matter of law.

The surface modifications are beneficial when the surface is wet with water or other liquid fluids. The micro-craters collect small pools of liquid which, in turn, provide additional lubricity. This is advantageous in medical, personal care, and cosmetic care applications, for example.

Figure 4:
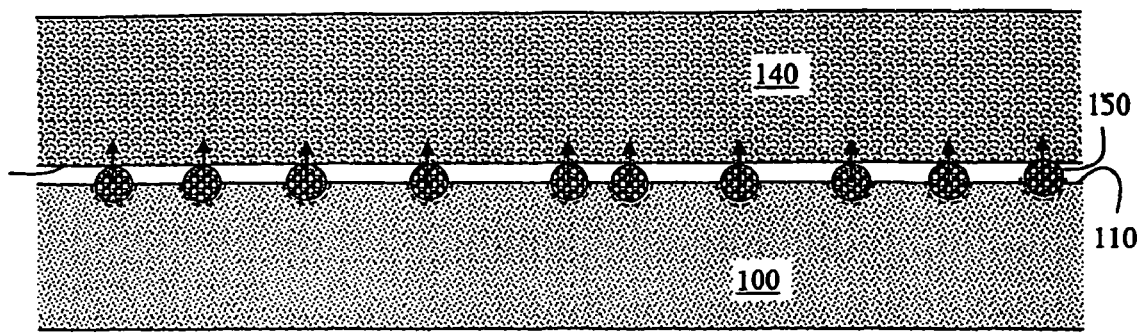
FIG. 4 is a side-elevated, partially sectional diagrammatic view of the elastomer surface illustrating the migration of compounds from the surface of the elastomer to overlaying tissue according to an embodiment of the invention.

The surface modification techniques disclosed herein may also be harnessed to transport compounds beneficial to the skin or other human tissue to the surface of the elastomer providing therapeutic or cosmetic benefits to such skin or other issue. As shown in FIG. 4, permeable tissue target 140 having tissue surface 145 abuts molded surface 110 wherein therapeutic compound 150 embedded in micro-craters 120 migrates through tissue surface 145 to deliver compound 150 to tissue target 140. Therapeutic compounds may be applied to molded surface 110 and retained by the micro-craters 120 for contact with tissue target 140. Such compounds may include, but are not limited to, vitamins, nutrients, antibiotics, antimicrobials, fungicides, cancer chemotherapeutics, and other drugs.

The elastomers of the present invention can be molded or extruded or thermoformed into various shapes and items such as prosthetic liners and sleeves, external breast prostheses, seals for CPAP (Continuous Positive Air Pressure) masks or other masks, headbands, burn treatment dressings, other wound care dressing sheets and pads, scar reduction pads, socks for diabetic feet, malleolus pads, metatarsal pads, shoe insoles, other orthotics, garments, catheters and balloons for catheters, temporary implantations, and applications of cosmetics.

5.2 Applications for Wound Healing

The thermoplastic elastomers of the present invention include antioxidants and hydroxyl scavengers as additives, and are formed into useful articles for wound healing applications.

In some embodiments, a thermoplastic elastomer includes one or more antioxidant and/or hydroxyl scavenger additives, for example, Irganox 1010 and/or other additives such as those listed in Table 1 above. Such additives can act as effective scavenges of free radicals and hydroxyl groups, and may have a beneficial effects on the skin, including for example, wound healing. Antioxidant additives such as Irganox 1010 have been previously used in thermoplastic polymers to scavenge oxygen and other free radicals that may degrade the polymers when they are in a molten state for molding and extrusion.

In the present invention, an excessive amount of such antioxidants are utilized; for example in an amount beyond the solubility of the antioxidant in the thermoplastic elastomer. In the polymer at room temperature, this excess, over time, precipitates out of the bulk of the polymer. Specifically, in a thermoplastic elastomer comprising mineral oil and a styrenic triblock copolymer, Irganox 1010 is added in excess of its room temperature solubility in the gel, precipitates in the build of the polymer, then migrates to the surface of the gel. In some embodiments, the mineral oil may also migrate to the surface of the gel and includes the additive (e.g., Irganox 1010) dissolved within the oil. The mineral oil penetrates into the skin of the user and carries with it the Irganox 1010 and/or other additives. Such thermoplastic elastomers may be used, for example, as liners or sleeves in prosthetic devices, as bandages, patches, pads, wound dressings, or in any other applications involving prolonged contact of an elastomer with the skin of a user, and in particular where healing of a wound is desired. The patient or user can be human or non human mammals, e.g., primate, dog, cat, mouse, cow, etc.

In preferred embodiments, the precipitated additives comprise antioxidants or free radical scavengers that are useful in treating different types of wounds, e.g., lesions due to burns, trauma, surgery, diabetic lesions or ulcers, pressure ulcers, etc. A therapeutic article such as a sleeve, liner, bandage, dressing, pad, malleolus pad, scar patch, insole or other article can include a thermoplastic elastomer with one or more additives as described herein. A fabric or other backing may be integrated within or bonded to the article. The fabric may be stitched or woven, and in some embodiments may be elastic in one or more directions and in other embodiments is substantially inelastic in one or more directions.

Examples of articles that include thermoplastic elastomer lining according to the present invention and that may be used for wound healing or scar repair include prosthetic liners, a prosthetic sleeve, a prosthetic skin, a burn dressing, a scar reduction pad, a wound care dressings, goggle frames, a mask, a headband, an orthotic device, a garment, a catheter, a temporary implantation, and a cosmetic application.

5.3 Prosthetic Devices Comprising Thermoplastic Elastomers

As mentioned above, the thermoplastic elastomers of the present invention are particularly suitable for use as liners, sleeves or other skin contact points in a prosthetic device. For example, referring to FIG. 13, a prosthetic liner 1300 is configured to receive and fit against a residual limb of an amputee patient, and to hold a prosthetic limb against the residual limb. For example, liner 1300 includes a thermoplastic elastomer 1312 with a fabric backing 1314 attached to one side. An inner surface 1315 of the thermoplastic elastomer preferably has microcraters as described herein and may include antioxidants, hydroxyl scavengers, antimicrobials, lubricants or other agents or substances that are applied to surface 1315 or precipitate from elastomer 1312. An open end 1302 is configured to receive the residual limb of the patient and a closed end 1304 is configured to attach to a prosthetic limb or other device. An umbrella 1316 or other device for securing the prosthetic limb is attached to or integrated within the liner 1300.

The fabric 1314 of liner 1300 may be any suitable fabric and may be stitched or woven. Fabric 1314 preferably allows stretching in a radial direction (e.g., radial stretching of up to 50%) and resists elongation (e.g., relatively inelastic in a longitudinal or axial direction to support the weight of a prosthetic limb).

Referring to FIGS. 14A and 14B, a prosthetic sleeve 1400 according to the present invention comprises a thermoplastic elastomer 1412 surrounded by a fabric 1414. Sleeve preferably is substantially cylindrical or conical in shape, and includes a central passage 1420 through which a limb or other body part may be placed. When sleeve 1400 is applied, inner surface 1415 contacts against the skin of the user. In embodiments where therapeutic agents are included in elastomer, such agents are transferred, e.g., by direct contact with the skin or through absorption of oil in the elastomer (e.g., where the therapeutic agent is carried by the oil). As described above, such sleeves or liners can be used to treat various types of wounds and/or infections, depending upon the additives in the composition of the thermoplastic elastomer.

One skilled in the art will appreciate that the thermoplastic elastomers of the present invention may be employed in various arrangements of know prosthetic devices. For example, additional details and examples of liners with which the thermoplastic elastomers of the present invention may be used can be found in U.S. Pat. No. 6,454,812 to Laghi and U.S. Pat. No. 4,923,474 Klasson et al., each of which is incorporated by reference herein in its entirety.

5.3 Elastomers Comprising Antimicrobial Additives (FIGS. 15-19)

The present invention provides methods of treating or preventing infection at a site by contacting the site using a thermoplastic elastomer of the invention, wherein the additive comprises an antimicrobial agent. In preferred embodiments, a thermoplastic elastomer comprises silver-based antimicrobial agents, provides a moisture barrier by being impermeable to water, and in its softer formulations, distributes pressure evenly on the skin surface and virtually eliminates shear forces on the skin.

An elastomer comprising one or more antimicrobial agents can be applied, for example, to a wound to treat or prevent an infectious agent such as a bacterium, a virus, a parasite, or a fungus.

A thermoplastic elastomer may be made as described above with respect to FIG. 1, wherein the additive 20 comprises one or more antimicrobial agents. For example, referring to FIG. 15, a process of making an elastomer includes combining antimicrobial agent 1520, plasticizing oil 1530, and polymer 1540 to form mixture 1550. Heat 1570 is applied to mixture 1550. Plasticizing oil 1530 may be heated prior to or after the addition of antimicrobial agent 1520 and polymer 1540. Mixture 1550 is melted in an extruder, a molding machine or other suitable heated vessel so that the antimicrobial agent 1520 become suspended in molten mixture 1550 and remains in stable suspension in the molten mixture. Molten mixture 1550 is molded 1560 into the form of a useful item to at an appropriate temperature. When allowed to cool, e.g., towards room temperature of approximately 25° C. the mixture solidifies and forms elastomer 1580. The antimicrobial agent 1520 begins to diffuse to the surface of the elastomer, preferably along with other microcrater-forming additives as described above with respect to FIG. 1. Upon completion of the solidification process, diffusion of the additives may be facilitated by seeding with talcum powder and/or imparting mechanical stresses on the elastomer 1580, as described above.

If the plasticizing oil is heated, an appropriate temperature range is about 130 to 165° F. Plasticizing oils such as paraffinic oils, naphtenic petroleum oils, mineral oils, and synthetic liquid oligomers of polybutene, polypropylene, polyterpene, and the like may be used. In some embodiments, 300 to 1,200 PPH of the plasticizing oil are used, more preferably between about 500 and 700 PPH.

The inert nature and antimicrobial efficiency of silver make it an attractive option for the present invention. It is not toxic, flammable or corrosive and will not cause bacteria to become resistant to antibiotics. Silver stops bacteria or fungi degrading the object's physical properties, and also prevents the build-up of harmful bacteria, which can be a source of infection to humans. Microorganisms such as bacteria, fungi and algae can affect the aesthetic and physical properties of an elastomer by causing black spotting or discoloration, odor and polymer degradation. And in hospitals and care homes where patients are particularly vulnerable to infection, the build up of bacteria such as methicillin-resistant *Staphylococcus aureus* (MRSA) can contribute to the spread of deadly infections.

An advantage of silver-based additives is that they can be used in high temperature processing. For example, silver zirconium phosphate is thermally stable up to 800° C. The anti-microbial agents are mixed either in the dry polymer or in the mixture of polymer and plasticizing oil.

TABLE 3

| | Chemical Name |
|---|---|
| 1 | Silver Zeolite |
| 2 | Silver Zirconium Phosphate |
| 3 | Silver Nitrate |
| 4 | Silver Thiosulfate |
| 5 | Silver Sulphadiazine |
| 6 | Silver Fusidate |
| 7 | Silver acetate |
| 8 | silver bromide |
| 9 | silver carbonate |
| 10 | silver chlorate |
| 11 | silver chloride |
| 12 | silver citrate |
| 13 | silver fluoride |
| 14 | silver iodate |
| 15 | silver lactate |
| 16 | silver nitrite |
| 17 | silver perchlorate |
| 18 | silver sulfide |

Silver-based antimicrobials use an ion exchange mechanism that slowly releases silver ions, which interact with the bonding sites on the microbe surface to prevent bacteria from reproducing. This slow, regulated release provides long-lasting effectiveness. In contrast, organic antimicrobials inhibit the growth of microbes by slowly leaching to the surface of the plastic, and subsequently into surrounding fluids. Such leaching can limit the durability of the additive and also cause discoloration and an unpleasant taste. In other embodiments, a quaternary ammonium compound (QAC) is used.

In some embodiments, approximately 100 parts by weight of triblock copolymer, 0.05 to 20 PPH of one or more antimicrobial agent, more preferably between about 0.25 and 20 PPH of antimicrobial agent, and 100 to 900 PPH of plasticizing oil, more preferably between about 500 and 700 PPH of plasticizing oil, are used. In some embodiments, an antioxidant is also added, for example about 2-4 parts of Irganox 1010, more preferably about 2.9-3.0 parts.

In other embodiments, an antimicrobial agent incorporated within a thermoplastic elastomer is a silver sodium hydrogen zirconium phosphate (e.g., AlphaSan RC 2000, Millken Chemical, Spartanburg, S.C.), which is a zirconium phosphate ion-exchange resin containing approximately 10% silver. In a preferred embodiment, AlphaSan RC 2000™ comprises approximately 0.5% to 5%, preferably between about 1% and 3%, more preferably about 2%, of the total weight of the polymer, plasticizer and additive formula. Optionally, a lubricant, ointment, or other substance may be added to the molded surface of the elastomer, and may be retained within the microcraters on the surface of the elastomer as described above.

Figure 16:
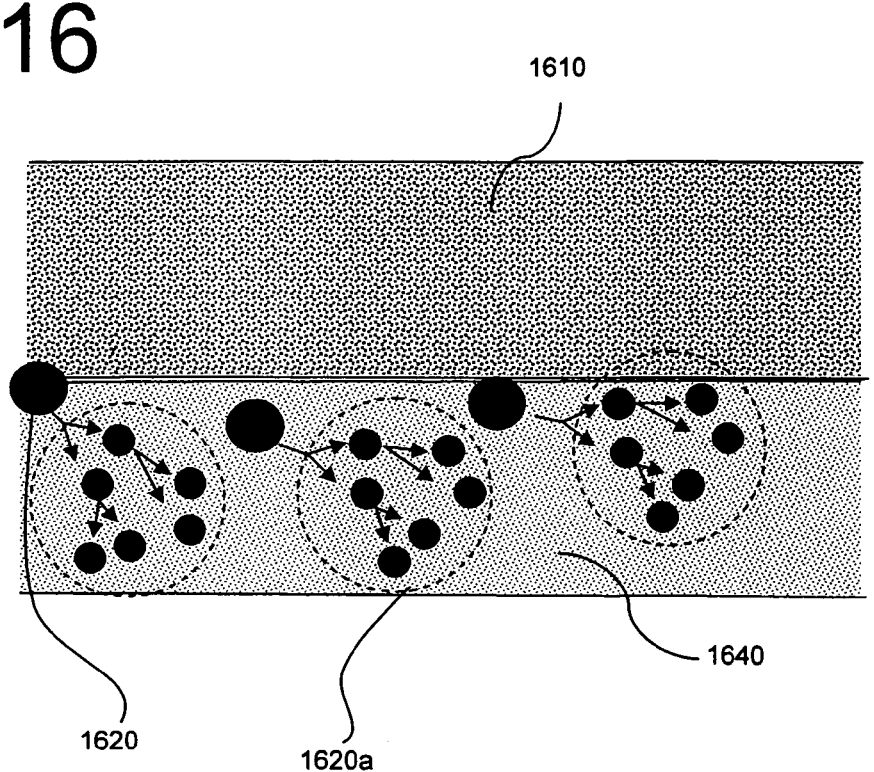
FIG. 16 is a side-elevated, partially sectional diagrammatic view of the elastomer surface in contact with an epidermal surface where no antimicrobial particles are used.
Figure 17:
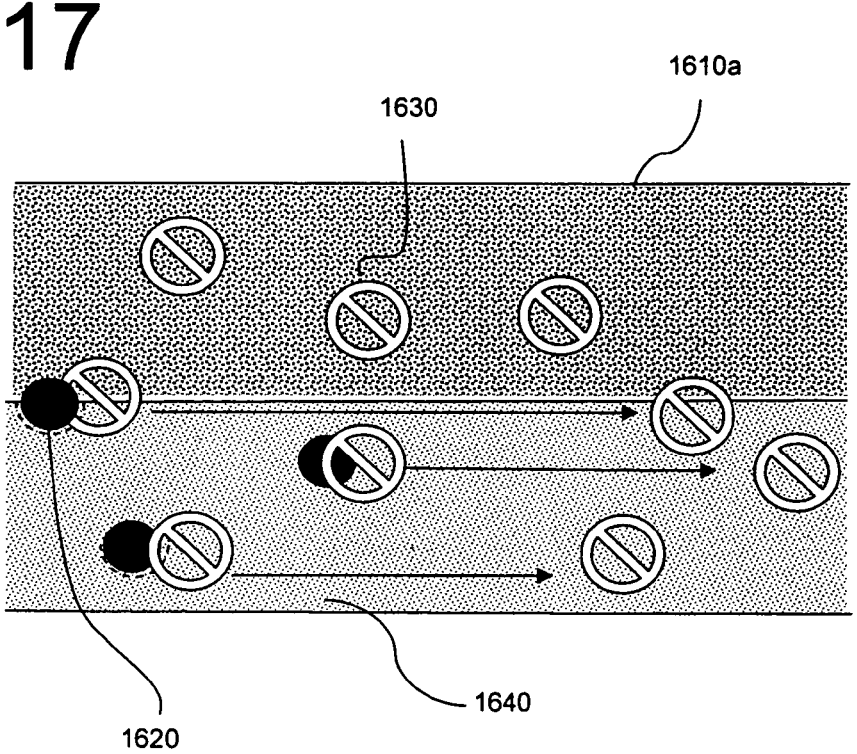
FIG. 17 is a side-elevated, partially sectional diagrammatic view of the elastomer surface in contact with an epidermal surface showing how antimicrobial particles of the present invention may interfere with microbial activity.

FIG. 16 illustrates the normal course of infection when conventional elastomers are used. As microbes 1620 encounter a hospitable environment, such as skin 1640, they begin to colonize. Microbes 1620 begin to multiply and exponentially colonize the area 1620a. In contrast, FIG. 17 shows that silver ions 1630 slowly migrate from elastomer 1610a toward tissue 1640. The positive charge of ions 1630 allows the silver ions to bond to the surface of microbes 1620, thus interrupting reproduction. Since microbes 1620 cannot reproduce, they eventually die and infection is thereby avoided. The silver ions are not consumed or dissolved in this process and therefore are able to continue their effectiveness.

Figure 18:
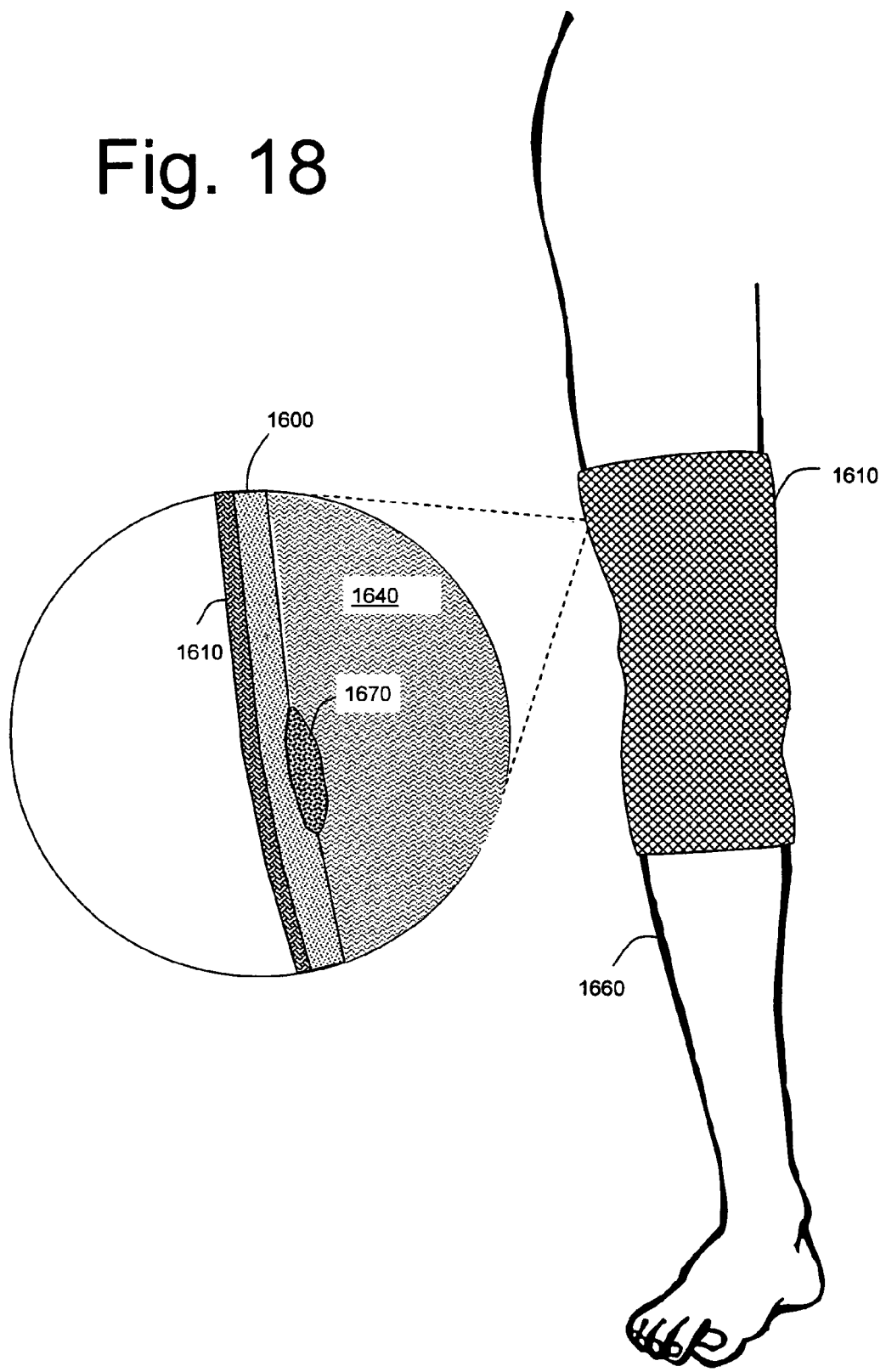
FIG. 18 is an elevated, magnified, partially sectional diagrammatic view of an embodiment of the invention as a sleeve around a wounded knee.
Figure 19:
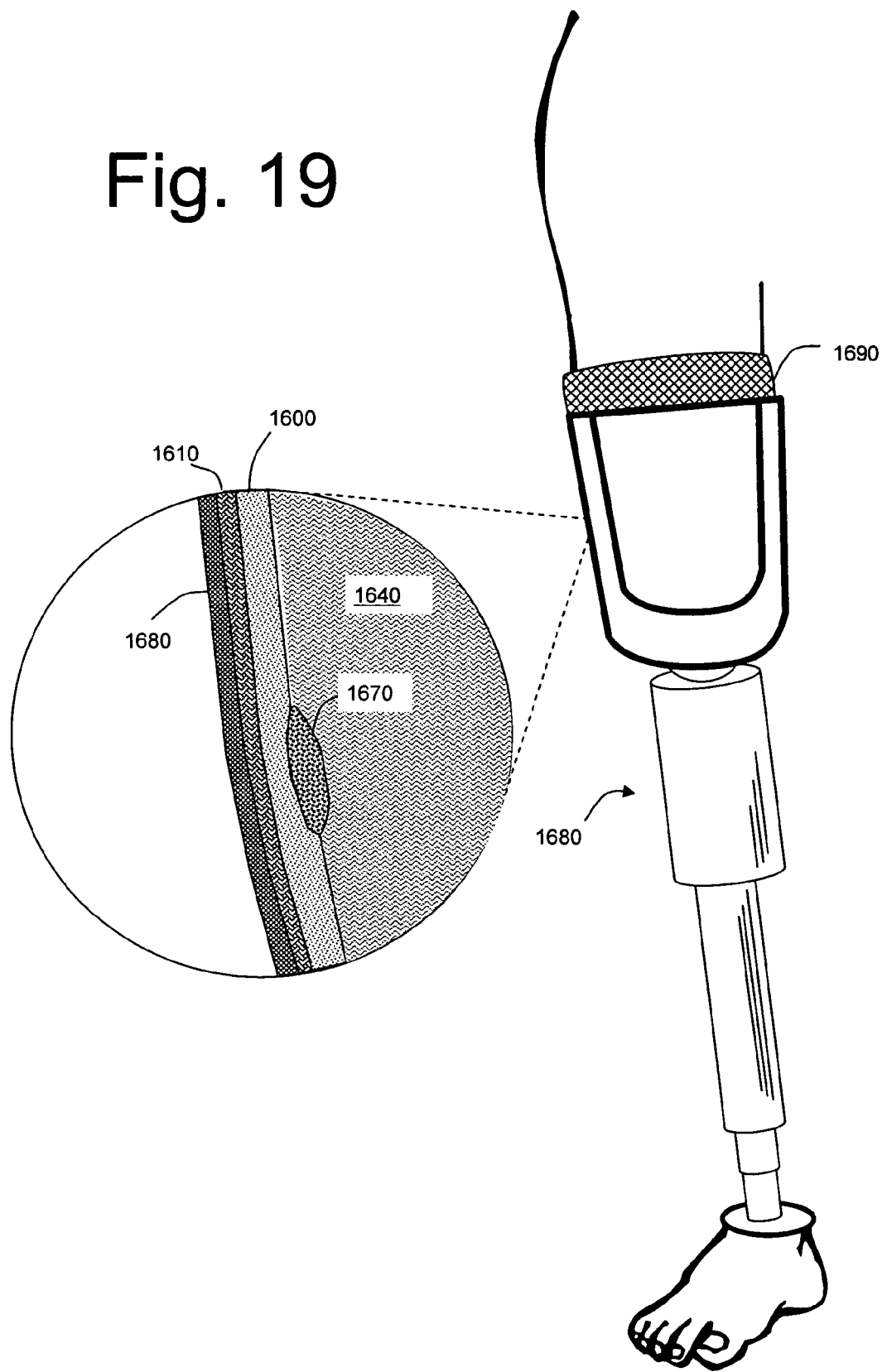
FIG. 19 is an elevated, magnified, partially sectional diagrammatic view of an embodiment of the invention as a prosthetic liner on a residual limb of an amputee.

FIGS. 18-19 show an application of the present invention. In FIG. 18, wound 1670 is located at the knee area of an individual's leg 1660. Molded surface 1610 of thermoplastic elastomer contacts wound 1670 whereby antimicrobial agent 1630 migrates from molded surface 1610 to wound 1670. In addition, the moisture impermeable properties of thermoplastic elastomer keep the wound area from drying out. Stretchable fabric 1610 keeps a predetermined pressure of on the wound to control edema and/or other disorders relating to pressure on tissue and wounds.

FIG. 19 illustrates the same principle but with prosthetic socket 1680 engaging leg 1660 by liner 1690 coated with thermoplastic elastomer on the inner surface of the fabric of the liner, in contact with wound 1670. As thermoplastic elastomer has all the properties of a prosthetic liner an additional advantage of the present invention is to prevent, stem or cure infections caused by previously ill-fitted prosthetic devices. Wounds and subsequent infections may occur when a user is improperly fitted with a prosthetic device, the user improperly deploys the device or the user's body has changed since the prosthetic device was originally designed. The present invention may be used to treat and prevent further infections, reduce friction and stress on the tissue of a prosthesis wearer by incorporating the thermoplastic elastomer into a liner, sleeve or any other situation wherein a elastomeric surface must abut or compress against tissue.

A case where antimicrobial thermoplastic elastomer for prosthetic liners is of particular advantage is that of post-operative prosthetic liners, as the opportunity for serious infections is more likely immediately after surgery when the surgical sutures are still fresh.

6.0 EXAMPLES 6.1 Thermoplastic Elastomer with Improved Surface Characteristics (FIGS. 6-12)

In an exemplary embodiment, thermoplastic elastomers were made having desired surface characteristics according to the procedure of FIG. 1, and included a polymer (Septon 4055), a plasticizing oil (Carnation 70 mineral oil) and an additive Irganox 1010. The Septon 4055 was added in an amount of 100 parts per hundred (about 15.4 pounds weight). The Carnation Mineral Oil was added in an amount of 525 parts, or 80.85 pounds. Irganox 1010 was added in an amount of 2.94 parts, or 0.453. Each thermoplastic elastomers created with this formulation were measured as shown and described below.

Prior to use, the Septon 4055 was stored in 15.4 pound bags and kept free of humidity. The Irganox 1010 was stored in 0.453 pounds (7.25 oz) bags and kept free of humidity. The mineral oil was stored in an oil reservoir and kept headed at 115 +2.5/−5.

During the mixing procedure, the mineral oil (80.85 pounds), was pumped into a polypropylene barrel and at 115 +2.5/−5°. The barrel is moved into the custom mixing machine (manufactured by ALPS South Corporation) and the Irganox 1010 (0.453 lbs) was poured into the oil. The mixture of oil and Irganox 1010 is mixed for about 10 minutes to create a solution. Once mixed, the solution temperature is measured to ensure it is less than 120°. If less, the Septon 4055 (15.4 lbs) was added to the solution and mixed for an additional 30 minutes.

For the molding process, a reciprocating screw was heated to about 115 +2.5/−5° F. The screw apparatus included injection hoses and cylinder. Nitrogen was introduced at into the polymer prior to entering the screw as a rate no less than 10 schf at 10 psi.

Core temperature of the melting apparatus comprised a screw nose that must be heated to approximately 390-425° F. Injection hose and cylinder equaled screw nose temperature, plus or minus approximately 5° F. Nitrogen was introduced into the polymer period to ensure the screw at a rate no less than 10 scfh at 10 psi (larger screws may require higher nitrogen settings).

The mold parameters were as follows: core temperature 85-95° F.; sleeve temperature 85-95° F.; base temperature was 85-95° F.; cooling water temperature was 60-65° F.; and cooling water flow rate was greater than 8 gpm.

In this example, the elastomer had a wall thickness of approximately 6 mm, and was cooled in approximately 100 seconds. (As described in Section 5.1 below, the amount of time required for injection and cooling of molten elastomer can vary depending upon the desired thickness of the elastomer).

After the elastomer was molded, the surface was coated with talcum powder to ensure the Irganox 1010 fell out of solution with the proper particle size. The part was staged on a post and the operator covered the entire surface by patting and rubbing the talcum powder into the part.

The part's surface aged over time as the Irganox 1010 migrated to the surface from within the polymer. The surface was noticeably changed after 24 hours. The Irganox 1010 continuously fell out over time until the solubility rate at end use temperature was reached.

Figure 6:
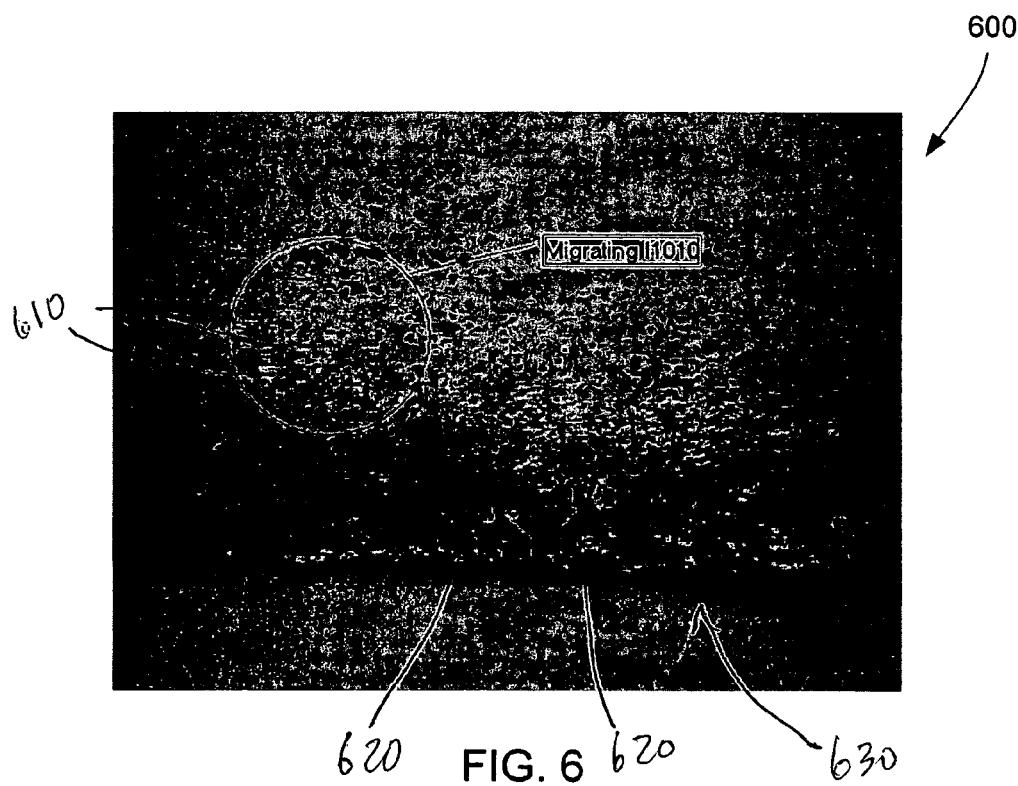
FIG. 6 is a photograph taken at 60× magnification of a cross-section of a thermoplastic elastomer showing hydroxyl scavengers migrating to the surface.

Referring to FIG. 6, a cross sectional photograph at 60× magnification shows an elastomer 600 with precipitated hydroxyl scavenger additives 610 forming in the gel medium, and microcraters 620 at the surface 630 of the elastomer. The precipitated additives 610 moved through the elastomer 600, creating microcraters 620 on surface 630. Therefore, the size of microcraters 620 is approximately equal to the size of the precipitated additive particles 610.

Figure 7:
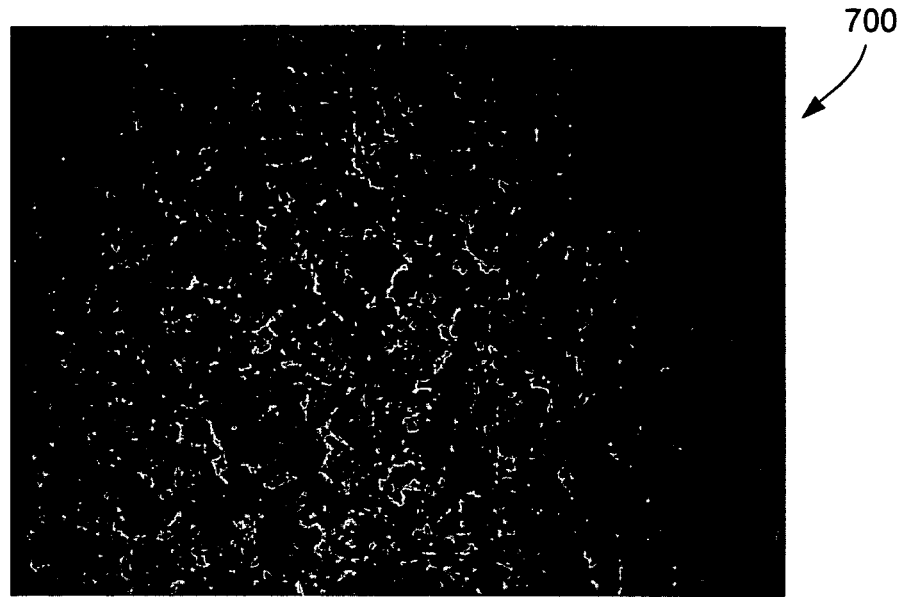
FIG. 7 is a top-view photograph of the modified surface of a thermoplastic elastomer, taken at 60× magnification.
Figure 8:
FIG. 8 is another top-view photograph of the modified surface of a thermoplastic elastomer, taken at 60× magnification.

FIG. 7 shows the surface of a cooled elastomer 700 that was formed according to the present invention and which includes hydroxyl scavengers tightly packed and relatively small in diameter. As stated above, the size of the scavenger precipitation spots is equal to the size of the craters. FIG. 8 is a similar top-view photograph of another elastomer 800 formed as described above, showing hydroxyl scavengers having larger diameters and more spaces in between.

Figure 9:
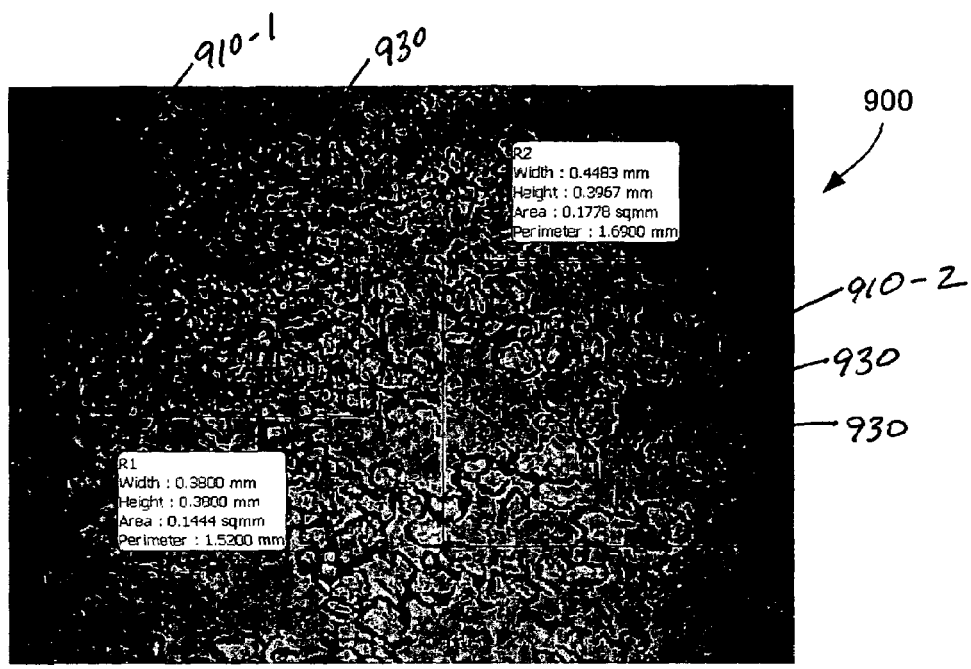
FIG. 9 is a top-view photograph of the modified surface of a thermoplastic elastomer after an aging process, taken a 60× magnification, and showing a desirable size and distribution of micro-craters.

The amount of microcraters in each of the formed elastomers was measured using a computer software as shown in FIG. 9. (Microscope: Skope by Boreal, Model 57900-01 with Motic DS-300 with 05×+PC camera; Software: Motic Diagro 2000, Motic China Group Ltd.) In particular, a box 910-1 and 910-2 was used to define an area, and the number of microcraters 930 in each area were counted. The following Table 4 shows the results of this procedure for the elastomer shown in FIG. 9.

TABLE 4

Microcraters per unit area in FIG. 9

|  | Width mm | Height mm | Area mm^2 | Perimeter mm | Microcraters in Area | Microcraters per mm^2 |
|---|---|---|---|---|---|---|
| Mean | 0.4335 | 0.4157 | 0.1807 | 1.6985 | 58.4444 | 329.7218 |
| Minimum | 0.3800 | 0.3750 | 0.1444 | 1.5200 | 39.0000 | 214.4035 |
| Maximum | 0.4667 | 0.4700 | 0.2170 | 1.8633 | 85.0000 | 517.3463 |
| StDev | 0.0276 | 0.0336 | 0.0230 | 0.1087 | 14.3362 | 102.8216 |

Figure 10:
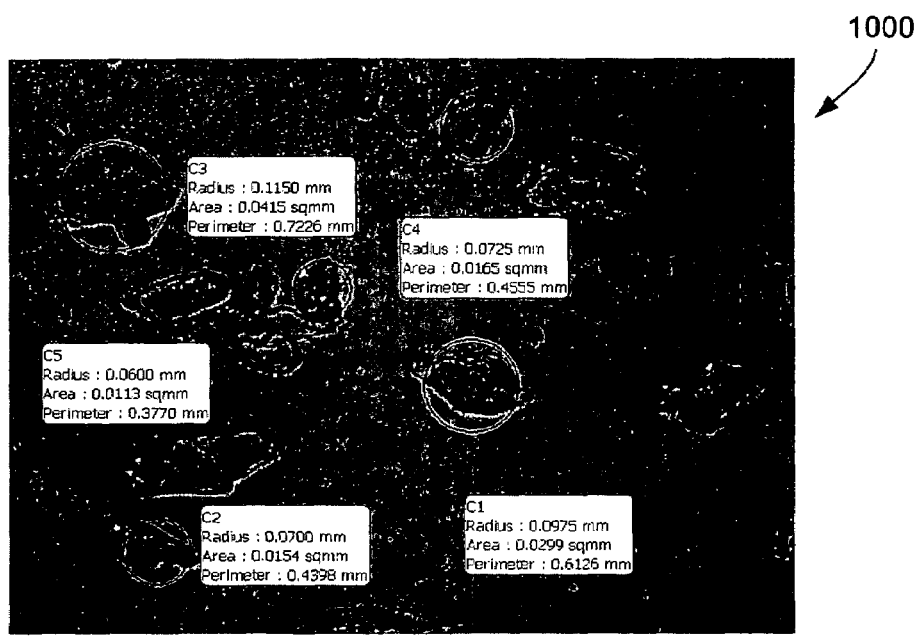
FIG. 10 is another top-view photograph of the modified surface of a thermoplastic elastomer after an aging process, taken a 60× magnification, and showing larger craters than FIG. 9.

FIG. 10 shows a top view photograph of an elastomer 1000 formed as described above, but where the process of precipitation of the hydroxyl scavengers was allowed to occurred slowly as no seeding, stretching, or other manipulations to facilitate precipitation were performed. In this example, the scavengers coagulated together to form crystals on the surface of the elastomer. The crystals made the surface rough, which is undesirable for use in some skin contact applications. The scavenger particle sizes in this example were 3 to 19 times larger than those on a more desirable surface, such as those shown in FIGS. 7-9. Such size measurements were performed, for example, using a computer program to draw an a circle, ellipse, or other shape around the outline of each crystal or crater, and to calculate the area, perimeter and radius of the defined area. The following table 5 includes measurement of the sizes of the microcraters formed in the elastomer of FIG. 10.

TABLE 5

Microcrater Size Measurements of FIG. 10

|  | Area mm^2 | Perimeter mm | Radius mm |
|---|---|---|---|
| Mean | 0.0199 | 0.4448 | 0.0708 |
| Max | 0.0616 | 0.8796 | 0.1400 |
| Min | 0.0005 | 0.0785 | 0.0125 |
| StDev | 0.0184 | 0.2331 | 0.0371 |

Figure 11:
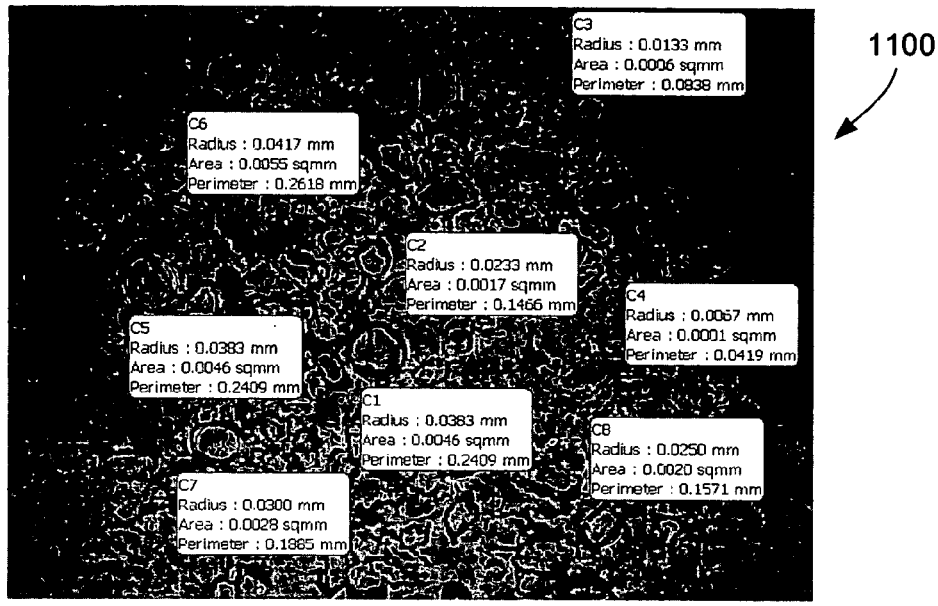
FIG. 11 is another top view photograph of the modified surface of a thermoplastic elastomer after an aging process, taken a 60× magnification, and showing additional measurements of micro-craters.

As shown in FIG. 11, similar area, perimeter, and radius measurements were made for other elastomers such as elastomer 1100. The following Table 6 provides area, perimeter and radius values for the hydroxyl scavengers of FIG. 10. As shown in Tables 5 and 6, The microcraters had a radius as small as 0.0001 mm or as large as 0.0616 mm. A preferred range is between about 0.0067 mm and 0.0433 mm.

TABLE 6

Microcrater Size Measurements of FIG. 11

|  | Area mm^2 | Perimeter mm | Radius mm |
|---|---|---|---|
| Mean | 0.0020 | 0.1472 | 0.0234 |
| Max | 0.0059 | 0.2723 | 0.0433 |
| Min | 0.0001 | 0.0419 | 0.0067 |
| StDev | 0.0015 | 0.0595 | 0.0095 |

Figure 12:
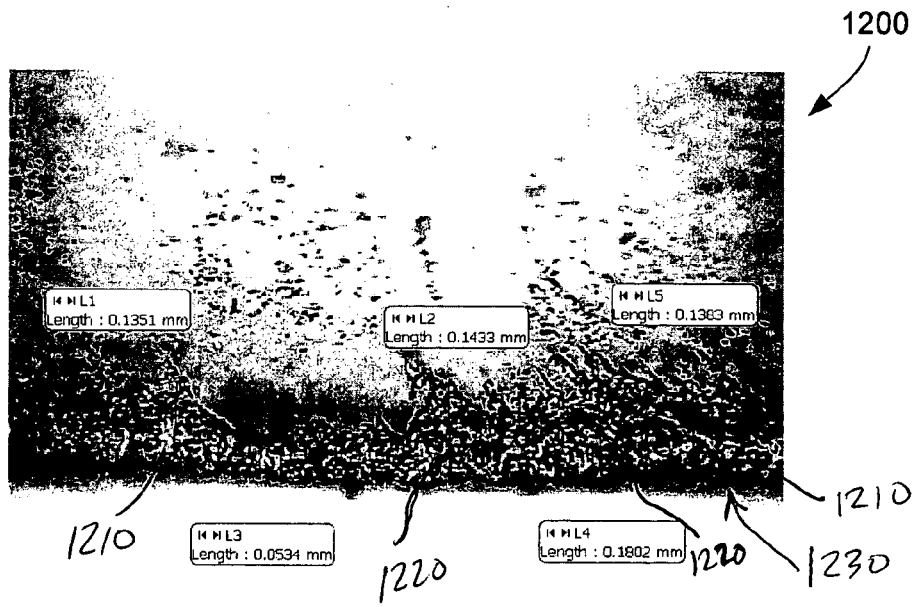
FIG. 12 is a cross-sectional side view photograph of a thermoplastic elastomer after migration of hydroxyl scavengers, taken 60× magnification, and showing measurements of surface characteristics.
Figure 15:
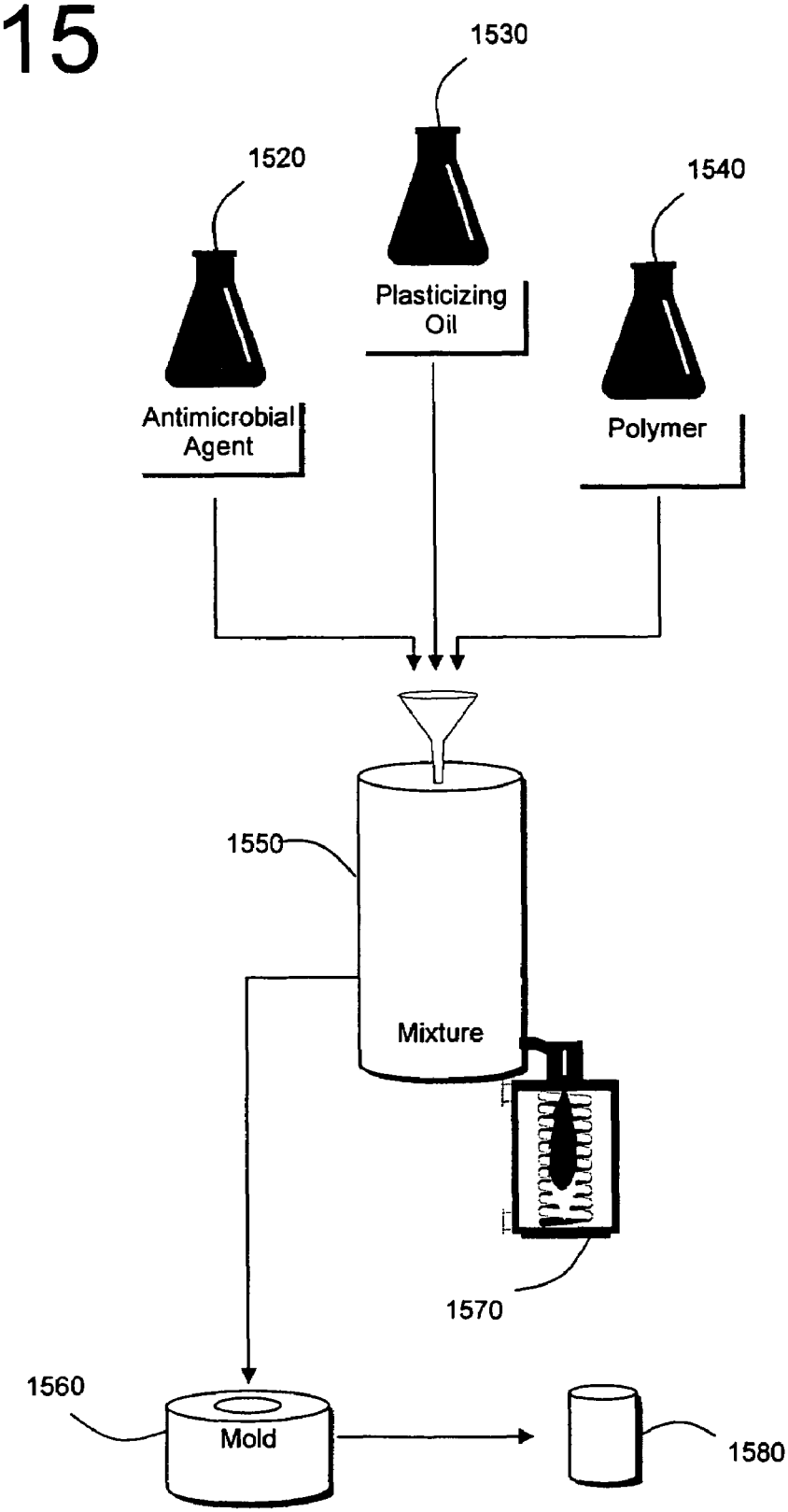
FIG. 15 is a diagrammatic view of a method of making a thermoplastic elastomer according to an embodiment of the invention.

Referring to FIG. 12, the depth of the microcraters and hydroxyl scavengers 1210 on the surface 1230 of a thermoplastic elastomer 1200 formed as described above according to the present invention was measured at various positions on the surface 1230 using lines 1220 drawn with the computer software. In the example of FIG. 12, the mean measured depth was 0.0634 mm, maximum depth was 0.143 mm, minimum depth was 0.0183, and the standard deviation of depth measurements was 0.0408 mm.

In another example, (tris(2,4-di-(tert)-butylphenyl)phosphite) (Irgafos 168™, Ciba Chemicals, Inc.) was used as the additive and formed the microcraters.

6.2 Liner with Hydroxyl Scavengers for Wound Healing

Figure 20A:
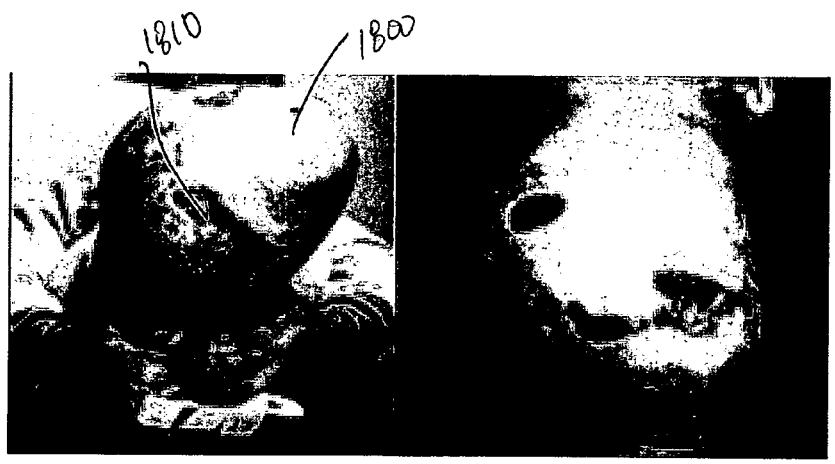
FIG. 20A is a photograph of the residual limb of an amputee patient having skin ulcers before fitting with a prosthetic liner comprising a thermoplastic elastomer of the present invention.
Figure 20B:
FIG. 20B is a photograph of the limb of the patient of FIG. 20A one week after fitting with the prosthetic liner comprising a thermoplastic elastomer of the present invention.
Figure 20C:
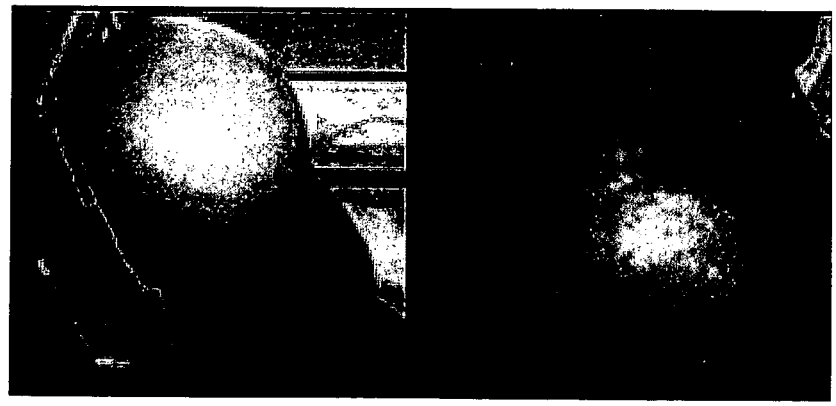
FIG. 20C is a photograph of the limb of the patient of FIG. 20A three weeks after fitting with the prosthetic liner comprising a thermoplastic elastomer of the present invention.

FIGS. 20A-20C show the effect of fitting a patient's limb having skin ulcers with a prosthetic liner (ALPS EasyLiner™, Alps South Corporation, St. Petersburg, Fla.). The liner comprised Septon 4055 and Carnation 70 mineral oil, and was supersaturated with Irganox 1010 to form microcraters according to the present invention.

FIG. 18A is a photograph showing skin ulcers 1810 on the leg 1800 of a patient prior to fitting with the thermoplastic elastomer liner. In this photograph, the patent had not donned her leg prosthesis for at least 3 weeks, and was being treated with a standard protocol of wet and dry dressings. The patient was then fitted with a prosthesis comprising the thermoplastic elastomer, which creating a suction suspension system. Once fitted with the prosthesis, the patient donned the prosthesis each morning, wore the prosthesis on the affected limb during the day (e.g., for approximately 8 to 14 hours at a time), and removed the prosthesis before sleeping going to bed each night.

FIG. 18B shows the limb one-week after being fitted with the prosthesis. The skin ulcers 1810 from FIG. 18A are visibly healing. By three weeks after the initial fitting, the skin ulcers 1810 appear to be completely healed as shown in FIG. 18C.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of making an elastomeric article and cratering the surface of said article, said method comprising the steps of: mixing together a mineral oil, a polymer that together with said mineral oil can form a thermoplastic elastomer, and a predetermined amount of at least one additive to form a mixture; the predetermined amount of additive being in excess of an amount of additive that is soluble in the mixture at room temperature; increasing the temperature of the mixture to at least a melting point where the mixture becomes molten and the additive is soluble in the molten mixture in a stable solution; and allowing the mixture to cool to form an elastomer under conditions whereby the additive precipitates and migrates to the surface of the elastomer, leaving microcraters on the surface of the elastomer.

2. The method of claim 1, further comprising the step of mechanically deforming the cooled mixture to facilitate precipitation of the additive from the elastomer.

3. The method of claim 1, wherein the additive comprises an antioxidant.

4. The method of claim 3, wherein the additive is selected from a group consisting of Tetrakis(2,4-di-tert-butylphenyl) [1,1-biphenyl]-4,4'-diylbisphosphonite; Tris(2,4-ditert-butylphenyl)phosphate; Butanedioic acid, dimethylester, hydroxy-2,2,6,6-tetramethyl-1-piperidine ethanol; 2,6-di-tert-butyl-4-(4,6-bis(octylthio)-1,3,5-triazin-2-ylamino)phenol; 3,3',3',5,5',5'-hexa-tert-butyl-a,a',a'-(mesitylene-2,4,6-triyl)tri-p-cre-sol; and Pentaerythritol Tetrakis(3-(3,5-di-tert-butyl-4-hydroxphenyl)propionate).

5. The method of claim 1, wherein the polymer is a block copolymer.

6. The method of claim 5, wherein the polymer is selected from a group consisting of poly(styrene ethylene ethylene propylene styrene), poly(styrene ethylene butylenes styrene), and poly(styrene ethylene propylene styrene).

7. The method of claim 1, wherein the at least one additive comprises an antimicrobial agent.

8. The method of claim 1, wherein the at least one additive comprises a silver salt or a quaternary ammonium compound.

9. The method of claim 7, wherein the antimicrobial agent is selected from the group consisting of elemental silver, silver oxides, silver salts, silver ion exchange compounds, silver zeolites, silver glasses, quaternary ammonium compounds, and mixtures thereof.

10. The method of claim 1, wherein the microcraters have a mean radius in the range of 0.001 to 0.07 mm.

11. The method of claim 10 wherein the microcraters have a mean radius of 0.0067 to 0.0433 mm.

12. The method of claim 10 or 11 wherein the microcraters have a mean depth of 0.01 to 0.2 mm.

13. The method of claim 10 or 11 wherein the microcraters have a mean depth of 0.0183 to 0.1434 mm.

14. The method of claim 1 wherein the microcraters are not visible to the naked eye having 20/20 vision.

15. The method of claim 1, which further comprises contacting the mixture with a precipitation seed after said allowing step.

16. The method of claim 15, wherein said precipitation seed is talcum powder.

17. The method of claim 1, which prior to said allowing step further comprises the step of molding the mixture into a chosen shape.

18. The method of claim 1 wherein said temperature is increased to 400 to 460 degree F. in said increasing step.

* * * * *